United States Patent [19]

James

[11] Patent Number: 5,080,798
[45] Date of Patent: Jan. 14, 1992

[54] MONITORING OLIGOMERS IN A POLYMER

[75] Inventor: David E. James, Batavia, Ill.

[73] Assignee: Amoco Corporation, Chicago, Ill.

[21] Appl. No.: 555,766

[22] Filed: Jun. 25, 1990

[51] Int. Cl.$^5$ .............................................. B01D 15/08
[52] U.S. Cl. ................................ 210/656; 73/61.1 C; 210/198.2; 210/635; 264/184
[58] Field of Search ............ 210/634, 635, 656, 198.2, 210/659; 73/61.1 C, 61.1 R; 264/184, 49; 585/458; 502/168, 185; 8/130.1; 435/4, 5; 430/195, 152; 436/546, 161, 178, 85, 8; 252/301.21; 562/487

[56] References Cited

U.S. PATENT DOCUMENTS

| | | | |
|---|---|---|---|
| 4,147,552 | 4/1979 | Specht et al. | 430/152 |
| 4,352,745 | 10/1982 | James et al. | 210/656 |
| 4,895,660 | 1/1990 | Kershner et al. | 210/640 |
| 4,968,471 | 11/1990 | Ito et al. | 264/184 |

FOREIGN PATENT DOCUMENTS 214693 10/1984 Fed. Rep. of Germany .

OTHER PUBLICATIONS

Snyder, L. R. and Kirkland, J. J., *Introduction to Modern Liquid Chromatography*, New York, 1979 pp. 552–554.

Primary Examiner—Robert A. Dawson
Assistant Examiner—Sun Uk Kim
Attorney, Agent, or Firm—Gunar J. Blumberg; William H. Magidson; Ralph C. Medhurst

[57] ABSTRACT

There are provided methods for monitoring the oligomeric content of prepolymers and polymers, which methods employ high-performance liquid chromatographic techniques. Typically, the methods of the present invention may be used to determine the oligomeric content of polyethylene terephthalate polymers and prepolymers.

22 Claims, 1 Drawing Sheet

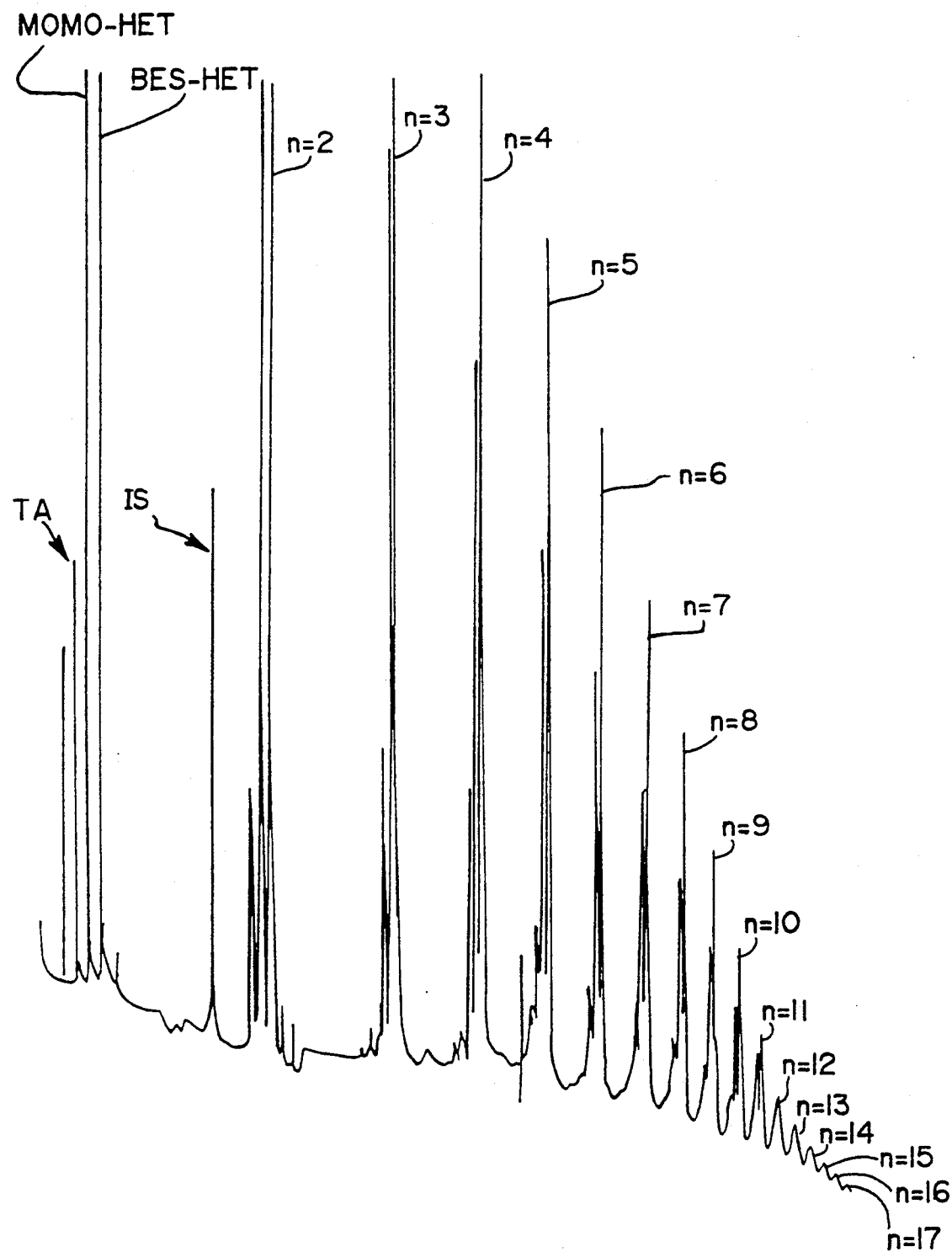

MONITORING OLIGOMERS IN A POLYMER

BACKGROUND OF THE INVENTION

1. Field of the Invention

This invention relates to liquid chromatography and its use for determining the oligomeric content of prepolymers and polymers. More particularly, it relates to a reversed-phase, high-performance liquid chromatographic method for the monitoring of the oligomeric content in polyethylene terephthalate prepolymer and polymer.

2. Description of the Prior Art

In German Democratic Republic Patent No. 214,693, Bogatzki et al., disclosed a quantitative liquid chromatographic process for the determination of oligomers in polyalkylene terephthalates. Reversed-phase chromatography was used to quantify the levels of oligomers in polyethylene terephthalate and polybutylene terephthalate samples. According to the method, previously known solution and elution systems, such as fluorinated alcohols with a specific water content, which dissolved the alkylene terephthalate molecules but allowed all molecules to pass through a UV detector and included the absorption of all molecules in the analysis, were used; the UV absorption of all alkylene terephthalate molecules was equated, resulting in the area of the peak(s) corresponding to the mass fraction and the peak identification being performed on the basis of synthesis of an oligomer series, and the influence of end group reactions on the location of the peaks was noted.

In Japanese Kokai Tokkyo Koho 81 12,551, Teijin Ltd. disclosed the injection of a polyester solution in a fluorine-containing alcohol, such as hexafluoroisopropanol, and chloroform into a gel permeation chromatographic column and elution with chloroform to determine molecular weight distribution accurately.

In Japanese Kokai Tokkyo Koho Japan 62,116,257 (87,116,257), Kanzaki, et al, disclosed that polyethylene terephthalate may be analyzed with good reproducibility by dissolving the polyesters or their oligomers in mixtures of chloroform and hexafluoroisopropanol and fractionating by gel permeation chromatography with elution by mixtures of chloroform with hexafluoroisopropanol and ethylene glycol.

From time to time, it becomes necessary to ascertain the oligomeric content of a poly(ethylene terephthalate) sample. For example, the presence of dicarboxylic acid-substituted, low-molecular weight oligomers of terephthalic acid and ethylene glycol could be a cause of plugging of spin-pack filters employed in the manufacture of textile yarns from purified terephthalic acid. Such plugging is undesirable, since it results in a process interruption. Knowing the oligomer content of the polyethylene terephthalate sample would be beneficial.

A method has been developed to monitor the prepolymer and the polymer. The method was used to investigate the above problem and was instrumental in showing a definite relationship between oligomer content and filter plugging.

SUMMARY OF THE INVENTION

According to the present invention, there is provided a method for monitoring the oligomeric content of a prepolymer by means of high-performance liquid chromatographic (HPLC) equipment, which method comprises dissolving a sample of said prepolymer in a solution comprising a fluorine-containing alcohol and dichloromethane to form a first solution, adding an internal standard solution to said first solution to form a second solution, diluting said second solution with dichloromethane to provide a diluted second solution, and immediately injecting said diluted second solution into said HPLC equipment.

There is provided also a method for monitoring the oligomeric content of a polymer by means of HPLC equipment, which method comprises dissolving a sample of said polymer in a solution comprising a fluorine-containing linear alcohol and dichloromethane to form a first solution, adding an internal standard solution to said first solution to form a second solution, diluting said second solution with dichloromethane to provide a diluted second solution, adding acetonitrile dropwise to said diluted second solution to effect precipitation of high-molecular weight polymer and produce a slurry, filtering said slurry to produce precipitated polymer and filtrate, and immediately injecting said filtrate into said HPLC equipment.

BRIEF DESCRIPTION OF THE FIGURE

The accompanying FIGURE represents a chromatogram obtained from a sample of a prepolymer of polyethylene terephthalate by means of HPLC equipment.

DESCRIPTION AND PREFERRED EMBODIMENTS

A method for determining the oligomers in polyethylene terephthalate wherein rapid sample preparation and acceptable reproducibility are present was needed. The method of the present invention was developed to fulfill this need.

The method of the present invention is suitable for monitoring the oligomeric content of a prepolymer. When it is used to determine the oligomeric content of a prepolymer, the method, which employs HPLC equipment, comprises dissolving a sample of said prepolymer in a solution comprising a fluorine-containing alcohol and dichloromethane to form a first solution, adding an internal standard solution to said first solution to form a second solution, diluting said second solution with dichloromethane to provide a diluted second solution, and immediately injecting said diluted second solution into said HPLC equipment.

In addition, the method may be used conveniently to monitor the oligomeric content of a polymer. For monitoring the oligomeric content of a polymer, the method comprises dissolving a sample of said polymer in a solution comprising a fluorine-containing linear alcohol and dichloromethane to form a first solution, adding an internal standard solution to said first solution to form a second solution, diluting said second solution with dichloromethane to provide a diluted second solution, adding acetonitrile dropwise to said diluted second solution to effect precipitation of high-molecular weight polymer and produce a slurry, filtering said slurry to produce precipitated polymer and filtrate, and immediately injecting said filtrate into said HPLC equipment.

Accordingly, the sample is prepared by dissolving the prepolymer or polymer in a mixture of hexafluoroisopropanol and dichloromethane to form a solution, if appropriate adding acetonitrile to the solution in order to precipitate high-molecular weight polymer from the solution, and immediately and directly injecting the second solution into the sample loop of the selected chromatographic column.

Suitable chromatographic equipment was employed in the tests described hereinafter. The equipment comprised a Spectra-Physics Model 8700 Solvent Delivery System, a DuPont Instruments Column Oven set at a temperature of 50° C. (122° F.), a Valco Model C6U Injection Valve equipped with a 10 microliter sample loop, a DuPont Zorbax ODS column having a length of 25 cm and an inside diameter of 4.6 mm, and a Waters Model 440 Absorbance Detector (254 nanometers and 0.05 aufs). A Spectra-Physics Model 4200 Computing Integrator was employed in performing peak area integration.

The mobile phase composition gradient that was employed for the separation is presented hereinafter in Table 1. Solvent A was a 1.0% aqueous HPLC-grade acetic acid, and Solvent B was HPLC-grade acetonitrile.

TABLE I

MOBILE PHASE COMPOSITION GRADIENT

| Time, min | A, vol % | B, vol % | Flow Rate, ml/min |
|---|---|---|---|
| 0 | 80 | 20 | 1.5 |
| 60 | 0 | 100 | |
| 65 | 0 | 100 | |
| 75 | 80 | 20 | |
| 77 | 80 | 20 | |

It is important that high-purity HPLC-grade solvents be used for the separation. Suitable HPLC-grade acetonitrile was obtained from Burdick and Jackson Laboratories, Inc., while HPLC-grade glacial acetic acid was obtained from J. T. Baker Chemical Company. Water was distilled and deionized and carbon-treated subsequently by means of a Millipore Milli-2 Purification System obtained from the Millipore Corporation.

SAMPLE PREPARATION

Each of the samples was prepared according to one of the following techniques.

For each prepolymer sample, the sample is dissolved in 1,1,1,3,3,3-hexafluoroisopropanol (HFIP) solution to form a first solution. An internal standard solution made up of 7-methoxycoumarin dissolved in dichloromethane is added to the first solution to make a second solution. Additional dichloromethane is added to the second solution to form a third solution and it is the third solution that is injected into the sample loop of the HPLC equipment.

For each polymer sample, the sample is dissolved in HFIP solution to form a first solution. An internal standard solution prepared by dissolving 7-methoxycoumarin in dichloromethane is added to the first solution to make a second solution. Dichloromethane is added to the second solution to form a third solution. Then acetontrile is added dropwise with stirring to effect precipitation of high-molecular weight polymer. The resulting slurry is filtered to remove the precipitated polymer, and the filtrate is injected into the sample loop of the HPLC.

The above summaries of sample preparations do not provide amounts of items used. In the case of each of the solvents, e.g., methanol and dichloromethane, a minimum amount of at least 60 µl is needed to ensure proper purging of the injection value. Typical values of chemicals and solutions employed for testing either the prepolymer or polymer are presented hereinafter in the examples.

INJECTION PROCEDURE

One of the key features of the methods of the present invention is the procedure that is used for sample injection. In the case of the following examples, the sample injection valve was placed in the "load" position and was flushed first with 1,000 microliters (µl) of methanol, followed by 1,000 µl of dichloromethane. Then the polymer sample was injected into the sample loop by means of a 500-µl syringe. After injection, with the valve still in the "inject" position, the system was flushed with 500 µl of dichloromethane.

Since changes in component concentrations occur with time, it is extremely important that the sample be injected into the sample loop of the column immediately after its preparation.

The method of the present invention, which employs reversed-phase high-performance liquid chromatography, was developed first to monitor the oligomer content of prepolymers and was amplified subsequently to analyze the oligomer content of high-molecular weight polymers, e.g., polyethylene terephthalate. The method of the present invention is illustrated hereinafter in the following examples.

These examples are presented to facilitate an understanding of the method of the present invention. Moreover, they are presented for the purpose of illustration and are not intended to limit the scope of the present invention which scope is to be limited solely by the appended claims.

EXAMPLE I

A prepolymer obtained from the esterification of terephthalic acid with ethylene glycol was evaluated.

A 0.1-gm specimen of the prepolymer was dissolved in 10 ml of a HFIP solution containing 30 wt % HFIP and 70 wt % dichloromethane to prepare Solution No. 1. Then 20 ml of the internal standard solution, which had been prepared by dissolving 0.100 gm of 7-methoxycoumarin in sufficient dichloromethane to make 100 ml of solution, was added to Solution No. 1 and the resulting solution, Solution No. 2, was diluted to 100 ml by the addition of dichloromethane to form Solution No. 3. A 1-ml portion of Solution No. 3 was diluted to 10 ml by the addition of dichloromethane to form Solution No. 4. A 10-µl portion of this latter solution was injected directly into the column of a high-performance liquid chromatographic instrument described hereinabove.

The mobile-phase gradient varied from 80 vol % aqueous 1.0 vol % acetic acid/20 vol % acetonitrile to 0 vol % aqueous 1.0 vol % acetic acid/100 vol % acetonitrile in 60 min. The flow rate was 1.5 ml/min and the column temperature was 50° C. (122° F.).

The chromatogram obtained from this prepolymer sample is represented in the accompanying FIGURE. From the injection of synthetic samples, the first three peaks in the chromatogram were determined to be terephthalic acid (TA), mono-hydroxyethyleneterephthalate (MONO-HET), and bis-hydroxyethyleneterephthalate (BIS-HET), respectively.

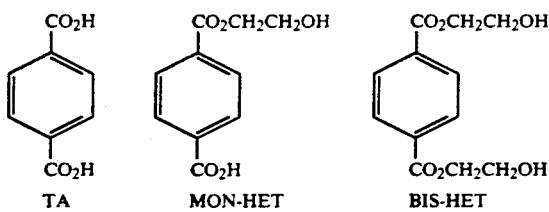

TA     MON-HET     BIS-HET

Seventeen groups of three peaks are shown. Each group of three peaks which follows represents elution of the diacid, acid/ester, and diester containing one more monomer unit than the one preceding it. As the molecule becomes larger, resolution between the three different species, i.e., diacid, acid/ester, and diester, as well as between monomer units, becomes more difficult.

The results obtained from this example demonstrate that the method of the present invention can be used to identify the diacid, acid/ester, and diester species of oligomers present in a prepolymer sample obtained from the esterification of terephthalic acid with ethylene glycol.

EXAMPLE II

Three samples of commercially-prepared polyethylene terephthalate were analyzed by the method of the present invention. Each sample was used in the preparation of at least two HPLC specimen in order that reproducibility might be shown.

Each specimen was prepared as described hereinafter.

A 0.250-gm specimen of polyester was placed in a 125-ml, round-bottom flask. Then 20 ml of a solution containing 30 wt % HFIP and 70 wt % dichloromethane were added to the contents of the flask. When the polymer specimen had become dissolved, 5 ml of an internal standard solution were added by means of a pipette. The internal standard solution was prepared by dissolving 0.250 gm of 7-methoxycoumarin obtained from Aldrich Chemical Company in sufficient diclorometnane to make 250 ml of solution. Then 45 ml of dichloromethane were added to the flask contents followed by the addition of 25 ml of acetonitrile. The acetonitrile was added dropwise with stirring to effect precipitation of high molecular weight polymer. The contents of the flask were filtered through No. 42 Whatman filter paper and the filtrate was injected immediately into the sample loop of the HPLC equipment described hereinabove and in the manner described hereinabove. Again it is pointed out that it is extremely important that the sample be injected immediately after its preparation into the sample loop of the column, since changes in component concentrations occur with time.

The results of these analyses are presented hereinbelow in Table II.

TABLE II

REPEAT ANALYSES FOR OLIGOMER CONTENT PET

| Sample | Prep'n | Concentration, ppm | | | | |
|---|---|---|---|---|---|---|
| | | TA | MHET | $(TG)_1T$ | $(GT)_2$ | $(TG)_2T$ |
| 1 | 1-1 | 125 | 175 | 313 | 340 | 448 |
| 1 | 1-2 | 188 | 171 | 327 | 368 | 479 |
| 2 | 2-1 | 81 | 27 | 72 | 79 | 87 |
| 2 | 2-2 | 52 | 27 | 61 | 71 | 98 |
| 3 | 3-1 | 174 | 28 | 67 | 68 | 180 |
| 3 | 3-2 | 107 | 26 | 54 | 61 | 185 |
| 3 | 3-3 | 72 | 32 | 59 | 63 | 209 |
| 3 | 3-4 | 72 | 32 | 56 | 75 | 182 |
| 3 | 3-5 | 46 | 36 | 64 | 76 | 208 |
| 3 | 3-6 | 46 | 31 | 54 | 65 | 191 |
| 3 | 3-7 | 55 | 33 | 63 | 80 | 193 |
| 3 | Average | 81.7 | 31.1 | 59.6 | 69.7 | 192.6 |
| 3 | Std Dev | 45.8 | 3.3 | 5.2 | 7.3 | 11.8 |

The structures of the low-molecular weight, carboxylic end group-containing PET oligomers represented by the nomenclature in Table II are presented hereinbelow in Table III.

Response factors for TA and MHET were 0.1006 and 0.1018, respectively.

TABLE III

STRUCTURES OF PET OLIGOMERS IN TABLE II

| Table II Nomenclature | Structure |
|---|---|
| TA | 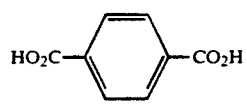 |
| MHET | 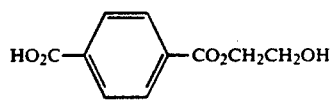 |
| $(TG)_1T$ | 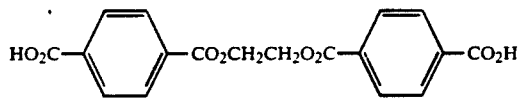 |
| $(GT)_2$ | 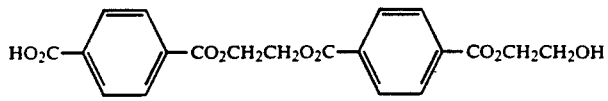 |

TABLE III-continued
STRUCTURES OF PET OLIGOMERS IN TABLE II

| Table II Nomenclature | Structure |
|---|---|
| (TG)$_2$T | HO$_2$C—⟨phenyl⟩—CO$_2$CH$_2$CH$_2$O$_2$C—⟨phenyl⟩—CO$_2$CH$_2$CH$_2$O$_2$C—⟨phenyl⟩—CO$_2$H |

The TA response factor multiplied by n (EXP 0.365) was used for the other diacids. Only the concentrations of carboxylic acid-containing oligomers are presented in Table II.

Please note that the sample with the high-oligomeric content, i.e., Sample 1, provided better reproducibility than the sample with low-oligomeric content, i.e., Sample 3.

As shown by the data in the preceding examples, oligomers having carboxylic acid end groups can be determined in a fairly reproducable manner by the method of the present invention.

What is claimed is:

1. A method for monitoring the oligomeric content of a prepolymer by means of high-performance liquid chromatographic (HPLC) equipment, which method comprises dissolving a sample of said prepolymer in a solution comprising a fluorine-containing linear alcohol and dichloromethane to form a first solution, adding an internal standard solution to said first solution to form a second solution, diluting said second solution with dichloromethane to provide a diluted second solution, and immediately injecting said diluted second solution into said HPLC equipment, said injecting being carried out via a technique comprising: (1) setting the injection valve in the load position; (2) with the injection valve in the load position, flushing said injection valve with at least 60 microliters ($\mu$l) of methanol and then with at least 60 $\mu$l of dichloromethane; (3) injecting said diluted second solution into the sample loop of said HPLC equipment; and (4) with the sample injection valve in the inject position, flushing said injection valve with at least 60 $\mu$l of dichloromethane.

2. The method of claim 1, wherein said fluorine-containing linear alcohol is hexafluoroisopropanol.

3. The method of claim 1, wherein said internal standard solution comprises 0.1 gm of 7-methoxycoumarin in sufficient dichloromethane to make 100 ml of solution.

4. The method of claim 1, wherein said prepolymer is a polyethylene terephthalate prepolymer.

5. The method of claim 2, wherein said internal standard solution comprises 0.1 gm of 7-methoxycoumarin in sufficient dichloromethane to make 100 ml of solution.

6. The method of claim 2, wherein said prepolymer is a polyethylene terephthalate prepolymer.

7. The method of claim 3, wherein said prepolymer is a polyethylene terephthalate prepolymer.

8. The method of claim 5, wherein a 0.1-gm sample of said prepolymer is dissolved in 10 ml of a solution comprising 30 wt % hexafluoroisopropanol and 70 wt % dichloromethane to form said first solution, 20 ml of said internal standard solution are added to said first solution to form said second solution, said second solution is diluted with dichloromethane to make 100 ml of diluted second solution, 1 ml of said diluted second solution is diluted to 10 ml with dichloromethane to form a test specimen, and 10 $\mu$l of said test specimen are injected into said HPLC equipment.

9. The method of claim 6, wherein said internal standard solution comprises 0.1 gm of 7-methoxycoumarin in sufficient dichloromethane to make 100 ml of solution.

10. The method of claim 9, wherein a 0.1-gm sample of said prepolymer is dissolved in 10 ml of a solution comprising 30 wt % hexafluoroisopropanol and 70 wt % dichloromethane to form said first solution, 20 ml of said internal standard solution are added to said first solution to form said second solution, said second solution is diluted with dichloromethane to make 100 ml of diluted second solution, 1 ml of said diluted second solution is diluted to 10 ml with dichloromethane to form a test specimen, and 10 $\mu$l of said test specimen are injected into said HPLC equipment.

11. The method of claim 10, wherein 1,000 $\mu$l of methanol and 1,000 $\mu$l of dichloromethane are employed to flush the injection valve in step (2) and 500 $\mu$l of dichloromethane are employed to flush the injection valve in step (4).

12. A method for monitoring the oligomeric content of a polymer by means of high-performance liquid chromatographic (HPLC) equipment, which method comprises dissolving a sample of said polymer in a solution comprising a fluorine-containing linear alcohol and dichloromethane to form a first solution, adding an internal standard solution to said first solution to form a second solution, diluting said second solution with dichloromethane to provide a diluted second solution, adding acetonitrile dropwise to said diluted second solution to effect precipitation of high-molecular weight polymer and produce a slurry, filtering said slurry to produce precipitated polymer and filtrate, and immediately injecting said filtrate into said HPLC equipment, said injecting being carried out via a technique comprising: (1) setting the injection valve in the load position; (2) with the injection valve in the load position flushing said injection valve with at least 60 $\mu$l of methanol and then with at least 60 $\mu$l of dichloromethane; (3) injecting said filtrate into the sample loop of said HPLC equipment; and (4) with the sample injection valve in the inject position, flushing said injection valve with at least 60 $\mu$l of dichloromethane.

13. The method of claim 12, wherein said fluorine-containing linear alcohol is hexafluoroisopropanol.

14. The method of claim 12, wherein said polymer is polyethylene terephthalate.

15. The method of claim 12, wherein said internal standard solution comprises 0.250 gm of 7-methoxycoumarin in sufficient dichloromethane to make 250 ml of solution.

16. The method of claim 13, wherein said polymer is polyethylene terephthalate.

17. The method of claim 13, wherein said internal standard solution comprises 0.250 gm of 7-methoxycoumarin in sufficient dichloromethane to make 250 ml of solution.

18. The method of claim 15, wherein said polymer is polyethylene terephthalate.

19. The method of claim 16, wherein said internal standard solution comprises 0.250 gm of 7-methoxycoumarin in sufficient dichloromethane to make 250 ml of solution.

20. The method of claim 17, wherein a 0.250-gm sample of said polymer is dissolved in 20 ml of a solution comprising 30 wt % hexafluoroisopropanol and 70 wt % dichloromethane to form said first solution, 5 ml of said internal standard solution are added to said first solution to form said second solution, 45 ml of dichloromethane are added to said second solution to form said diluted second solution, 25 ml of acetonitrile are added to said diluted second solution to precipitate said high-molecular weight polymer, and 20 µl of said filtrate are injected into said HPLC equipment.

21. The method of claim 19, wherein a 0.250-gm sample of said polymer is dissolved in 20 ml of a solution comprising 30 wt % hexafluoroisopropanol and 70 wt % dichloromethane to form said first solution, 5 ml of said internal standard solution are added to said first solution to form said second solution, 45 ml of dichloromethane are added to said second solution to form said diluted second solution, 25 ml of acetonitrile are added to said diluted second solution to precipitate said high-molecular weight polymer, and 20 µl of said filtrate are injected into said HPLC equipment.

22. The method of claim 21, wherein 1,000 µl of methanol and 1,000 µl of dichloromethane are employed to flush the injection valve in step (2) and 500 µl of dichloromethane are employed to flush the injection valve in step (4).

* * * * *

UNITED STATES PATENT AND TRADEMARK OFFICE
CERTIFICATE OF CORRECTION

PATENT NO. : 5,080,798
DATED : January 14, 1992
INVENTOR(S) : David E. James

It is certified that error appears in the above-identified patent and that said Letters Patent is hereby corrected as shown below:

| Col. | Line | |
|---|---|---|
| 8 | 51 | "position flushing" should read --position, flushing-- |

Signed and Sealed this

Twentieth Day of April, 1993

*Attest:*

MICHAEL K. KIRK

*Attesting Officer*     *Acting Commissioner of Patents and Trademarks*